(12) United States Patent
Engel et al.

(10) Patent No.: US 7,772,446 B2
(45) Date of Patent: Aug. 10, 2010

(54) METHOD FOR PRODUCING SUBSTITUTED BIPHENYLS

(75) Inventors: Stefan Engel, Nieder-Olm (DE); Tanja Oberding, Piquete-SP-Brasil (BR)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 11/885,247

(22) PCT Filed: Mar. 2, 2006

(86) PCT No.: PCT/EP2006/060400

§ 371 (c)(1),
(2), (4) Date: Aug. 28, 2007

(87) PCT Pub. No.: WO2006/092429

PCT Pub. Date: Sep. 8, 2006

(65) Prior Publication Data

US 2008/0183021 A1 Jul. 31, 2008

(30) Foreign Application Priority Data

Mar. 2, 2005 (DE) ........................ 10 2005 010 107

(51) Int. Cl.
*C07C 205/06* (2006.01)
*C07C 211/00* (2006.01)
(52) U.S. Cl. ...................................... 568/928; 564/305
(58) Field of Classification Search ................. 568/928; 564/305
See application file for complete search history.

(56) References Cited

U.S. PATENT DOCUMENTS

| | | | |
|---|---|---|---|
| 5,330,995 A | 7/1994 | Eichen et al. | |
| 5,480,897 A | 1/1996 | Eicken et al. | |
| 5,556,988 A | 9/1996 | Eicken et al. | |
| 5,589,493 A | 12/1996 | Eicken et al. | |
| 6,087,542 A | 7/2000 | Eicken et al. | |
| 6,362,380 B1* | 3/2002 | Eicken et al. | 568/933 |
| 2003/0100792 A1 | 5/2003 | Koch et al. | |
| 2009/0005597 A1* | 1/2009 | Smidt et al. | 564/307 |
| 2009/0030233 A1* | 1/2009 | Ehrenfreund et al. | 564/305 |

FOREIGN PATENT DOCUMENTS

| | | | |
|---|---|---|---|
| EP | 0 545 099 A | | 6/1993 |
| JP | 2001-55360 | | 2/2001 |
| JP | 2001-055360 | * | 2/2001 |
| JP | 2003-119175 A | | 4/2003 |
| WO | WO-97/33846 A1 | | 9/1997 |

OTHER PUBLICATIONS

Gilbert et al., Amide Bond Replacements: Incorporation of a 2,5,5-Trisubstituted Imidazoline into Dipeptides and into a CCK-4 Derivative, Tetrahedron Letters, vol. 32, No. 20, 1991, pp. 2277-2280.
Zapf et al., "Palladium/Phosphite Catalyst Systems for Efficient Cross Coupling of Aryl Bromides and Chlorides with Phenylboronic Acid," Chem. Eur. J., vol. 6, No. 10, 2006, pp. 1830-1833.
Grasa et al., "Suzuki-Miyaura Cross-Coupling Reactions Mediated by Palladium/Imidazolium Salt Systems," Organometallics, vol. 21, 2002, pp. 2866-2873.
Hassan et al., "Aryl-Aryl Bond Formation One Century after the Discovery of the Ullmann Reaction," Chem. Rev., vol. 102, 2002, pp. 1359-1469.
Zim et al., PdCl2(SEt2)2 and Pd(OAc)2: simple and efficient catalyst precursors for the Suzuki cross-coupling reaction, Tetrahedron Letters, vol. 41, 2000, pp. 8199-8202.
Dennis G. Hall, "Boronic Acids", Wiley-VCH, pp. 124-131, 2004.
Miyaura et al., "Palladium-Catalyzed Cross-Coupling Reactions of Organoboron Compounds", Chem. Rev. 1995, 95, pp. 2457-2483.

* cited by examiner

*Primary Examiner*—Shailendra Kumar
(74) *Attorney, Agent, or Firm*—Brinks Hofer Gilson & Lione

(57) ABSTRACT

A process for preparing substituted biphenyls

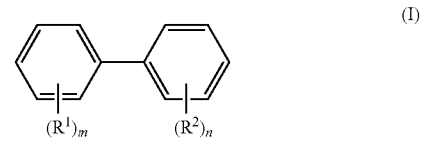

in which
$R^1$=nitro, amino or $NHR^3$,
$R^2$=CN, $NO_2$, halogen, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-alkylcarbonyl or phenyl,
$R^3$=$C_1$-$C_4$-alkyl, $C_2$-$C_4$-alkenyl or $C_2$-$C_4$-alkynyl,
m=1 or 2; n=0 to 3,
which comprises reacting a compound II

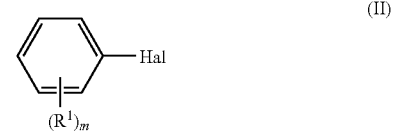

in the presence of a base and of a palladium catalyst selected from the group of: a) palladium-triarylphosphine or -trialkylphosphine complex with palladium in the zero oxidation state, b) salt of palladium in the presence of triarylphospine or trialkylphosphine as a complex ligand or c) metallic palladium applied to support if appropriate,
in the presence of triarylphosphine or trialkylphosphine, in a solvent, with a diphenylborinic acid (III)

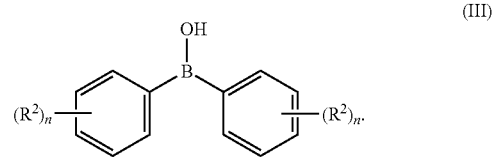

21 Claims, No Drawings

METHOD FOR PRODUCING SUBSTITUTED BIPHENYLS

This application is a 371 of PCT/EP2006/060400, filed Mar. 2, 2006.

The present invention relates to a process for preparing substituted biphenyls of the formula I

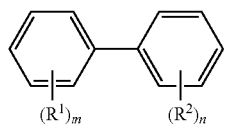

in which the substituents are defined as follows:

$R^1$ is nitro, amino or $NHR_3$, $R^2$ is cyano, nitro, halogen, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, ($C_1$-$C_6$-alkyl)carbonyl or phenyl, $R^3$ is $C_1$-$C_4$-alkyl, $C_2$-$C_4$-alkenyl or $C_2$-$C_4$-alkynyl, m is 1 or 2, where, in the case that m=2, the two $R^1$ radicals may have different definitions, n is 0, 1, 2 or 3, where, in the case that n=2 or 3, the two $R^2$ radicals may have different definitions, which comprises reacting a compound of the formula II

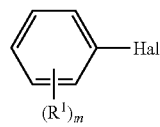

in which Hal is halogen and $R^1$ and m are each as defined above, in the presence of a base and of a palladium catalyst selected from the group of: a) palladium-triarylphosphine or -trialkylphosphine complex with palladium in the zero oxidation state, b) salt of palladium in the presence of triarylphospine or trialkylphosphine as a complex ligand or c) metallic palladium applied to support if appropriate, in the presence of triarylphosphine or trialkylphosphine, in a solvent, with a diphenylborinic acid (III)

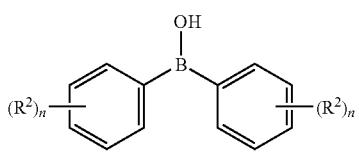

in which $R^2$ and n are each as defined above, where the triarylphosphines or trialkylphosphines used may be substituted.

Tetrahedron Lett. 32, page 2277 (1991) states that the coupling reaction between phenylboronic acid and chlorobenzene with use of the [1,4-bis(diphenylphosphine)-butane]palladium(II) dichloride catalyst proceeds with a yield of only 28%.

EP-A 0 888 261 discloses a process for preparing nitrobiphenyls by reacting chloronitrobenzenes with a phenylboronic acid in the presence of a palladium catalyst and of a base. In this process, a very high catalyst concentration is necessary.

It was therefore an object of the present invention to provide an economically viable process which can be implemented on the industrial scale for regioselectively preparing substituted biphenyls, which works with a reduced palladium catalyst concentration.

Accordingly, the process defined at the outset has been found.

The diphenylborinic acid (III) is obtained by reaction of optionally substituted phenylmagnesium chloride V with trialkyl borate, preferably trimethyl borate, in tetrahydrofuran as a solvent according to scheme 1 which follows.

Scheme 1:

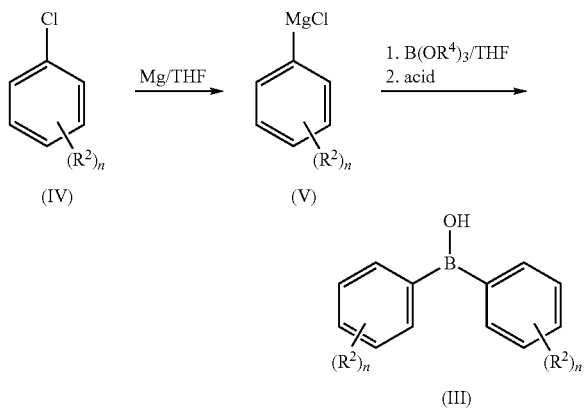

$R^4$ is $C_1$-$C_4$-alkyl, preferably methyl.

Essential for a high yield of diphenylborinic acid (III) is the use of only 0.7 eq. of trialkyl borate based on the chlorobenzene (IV) used. Use of about 1.1 eq. of trialkyl borate gives rise to phenylboronic acid as described in EP-A 0 888 261.

This reduction in the trialkyl borate use has several surprising advantages in relation to the preparation of nitrobiphenyls (I). The space-time yield is increased. The feedstock costs are lowered as a result of reduction in the amount of expensive trimethyl borate. Unlike the phenylboronic acids used in EP-A 0 888 261, the diphenylborinic acids (III) are soluble in tetrahydrofuran, which leads to an improvement in heat removal during the reaction, which is accompanied by lower consumption of the cooling capacity. This leads in turn to higher process safety.

The reaction temperature in this process stage is from 10 to 30° C., preferably from 15 to 25° C.

The substituted biphenyls prepared by the present process have the following preferred substituents:

$R^1$ nitro, amino, methylamino, propylamino, butylamino, allylamino or propargyl-amino, more preferably nitro, amino or methylamino, most preferably nitro or amino;

$R^2$ cyano, nitro, fluorine, chlorine, bromine, methyl, ethyl, propyl, butyl, allyl, propargyl, methoxy, ethoxy, trifluoromethyl or phenyl, more preferably fluorine, chlorine, methyl or methoxy, most preferably fluorine or chlorine;

$R^3$ methyl, ethyl, propyl, butyl, allyl or propargyl, more preferably methyl, ethyl or allyl, most preferably methyl;

m 1;

n 0, 1 or 2, preferably 0 or 1, most preferably 1.

The subsequent homogeneously catalyzed Suzuki biaryl cross-coupling is carried out according to scheme 2.

Scheme 2:

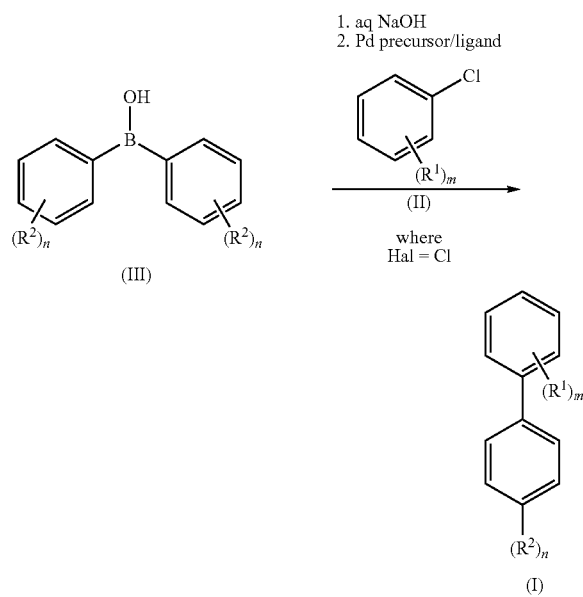

Preference is given to starting from diphenylborinic acids of the formula (III) in which $R^2$ and n are each as defined above.

Further preferred starting materials are diphenylborinic acids (III) in which n is 0 or 1 and is in particular 1.

Very particular preference is given to di(4-methylphenyl)borinic acid, di(4-fluorophenyl)-borinic acid and in particular di(4-chlorophenyl)borinic acid as the starting compound (III).

Preference is given to starting from compounds (II) which bear a single nitro or amino group (m=1), especially 4-nitrochlorobenzene or 4-aminochlorobenzene and in particular 2-nitrochlorobenzene or 2-aminochlorobenzene.

The compound (II) is used, based on the diphenylborinic acids (III) (diphenylborinic acid equivalents), normally in an equimolar amount, preferably with an up to 20 percent excess, preferably with an up to 50 percent excess.

The bases used may be organic bases, for example tertiary amines. Preference is given to using, for example, triethylamine or dimethylcyclohexylamine.

The bases used are preferably alkali metal hydroxides, alkaline earth metal hydroxides, alkali metal carbonates, alkaline earth metal carbonates, alkali metal hydrogen-carbonates, alkali metal acetates, alkaline earth metal acetates, alkali metal alkoxides and alkaline earth metal alkoxides, in a mixture and in particular individually.

Particularly preferred bases are alkali metal hydroxides, alkaline earth metal hydroxides, alkali metal carbonates, alkaline earth metal carbonates and alkali metal hydrogencarbonates.

Especially preferred bases are alkali metal hydroxides, e.g. sodium hydroxide and potassium hydroxide, and also alkali metal carbonates and alkali metal hydrogencarbonates, e.g. lithium carbonate, sodium carbonate and potassium carbonate.

The base is used in the process according to the invention preferably with a fraction of from 100 to 500 mol %, more preferably from 150 to 400 mol %, based on the diphenylborinic acids (III).

Suitable palladium catalysts are palladium-ligand complexes with palladium in the zero oxidation state, salts of palladium in the presence of complex ligands, or metallic palladium applied to support if appropriate, preferably in the presence of complex ligands.

Suitable complex ligands are uncharged ligands such as triarylphosphines and trialkylphosphines, which may optionally be substituted in the aryl rings, such as triphenylphosphine (TPP), di-1-adamantyl-n-butylphosphine, tri-tert-butylphosphine (TtBP) or 2-(dicyclohexylphosphino)biphenyl.

Furthermore, the literature has also described further particularly reactive complex ligands from other structural classes, including 1,3-bis(2,6-diisopropylphenyl)-4,5-H2-imidazolium chloride (cf., for example, G. A. Grasa et al., Organometallics 2002, 21, 2866) and tris(2,4-di-tert-butylphenyl) phosphite (cf. A. Zapf et al., Chem. Eur. J. 2000, 6, 1830).

The reactivity of the complex ligands can be enhanced by adding a quaternary ammonium salt such as tetra-n-butylammonium bromide (TBAB) (cf., for example, D. Zim et al., Tetrahedron Lett. 2000, 41,.8199).

If required, the water solubility of the palladium complexes can be improved by various substituents such as sulfonic acid or sulfonate salt groups, carboxylic acid or carboxylate salt groups, phosphonic acid, phosphonium or phosphonate salt groups, peralkylammonium, hydroxyl and polyether groups.

Among the palladium-ligand complexes with palladium in the 0 oxidation state, preference is given to using tetrakis(triphenylphosphine)palladium and additionally tetrakis[tri(o-tolyl)phosphine]palladium.

In the salts of palladium which are used in the presence of complex ligands, the palladium is normally present in the two positive oxidation state. Preference is given to using palladium chloride, palladium acetate or bisacetonitrilepalladium chloride. Particular preference is given to using palladium chloride.

In general, from 6 to 60, preferably from 15 to 25, equivalents of the aforementioned complex ligands, in particular triphenylphosphine and tri-tert-butylphosphine, are combined with one equivalent of the palladium salt.

EP-A 0 888 261 describes the use of from 2 to 6 equivalents of triphenylphosphine per equivalent of the palladium catalyst. The use of high ligand excesses is generally viewed in the literature as disadvantageous, since this is expected to result in inactivation of the catalytically active complex (cf., for example, J. Hassan et al., Chem. Rev. 2002, 102, 1359).

It was thus surprising that the high excess of complex ligand in combination with the low catalyst use led to an increase in the overall yield of the process of the present invention and accordingly to an improvement in the economic viability.

Metallic palladium is used preferably in pulverized form or on a support material, for example in the form of palladium on activated carbon, palladium on alumina, palladium on barium carbonate, palladium on barium sulfate, palladium on calcium carbonate, palladium on aluminosilicates such as montmorillonite, palladium on $SiO_2$ and palladium on calcium carbonate, in each case with a palladium content of from 0.5 to 12% by weight. In addition to palladium and the support material, these catalysts may comprise further dopants, for example lead.

When metallic palladium applied to support if appropriate is used, particular preference is given to also using the aforementioned complex ligands, in particular to the use of palladium on activated carbon in the presence of triphenylphosphine as a complex ligand, where the phenyl groups in the triphenylphosphine are preferably substituted by a total of from one to three sulfonate groups.

In the process according to the invention, the palladium catalyst is used with a low fraction of from 0.001 to 1.0 mol %, preferably from 0.005 to 0.5 mol % or from 0.01 to 0.5 mol % and in particular from 0.005 to 0.05 mol %, based on the compound (II).

The low use of a palladium salt in combination with a high use of complex ligand constitutes a significant cost advantage of this process over the prior art processes.

The process according to the invention may be carried out in a biphasic system composed of aqueous phase and solid phase, i.e. the catalyst. In that case, the aqueous phase may also comprise a water-soluble organic solvent in addition to water.

Organic solvents suitable for the process according to the invention are ethers such as dimethoxyethane, diethylene glycol dimethyl ether, tetrahydrofuran, dioxane and tert-butyl methyl ether, hydrocarbons such as n-hexane, n-heptane, cyclohexane, benzene, toluene and xylene, alcohols such as methanol, ethanol, 1-propanol, 2-propanol, ethylene glycol, 1-butanol, 2-butanol and tert-butanol, ketones such as acetone, ethyl methyl ketone and isobutyl methyl ketone, amides such as dimethylformamide, dimethylacetamide and N-methylpyrrolidone, in each case individually or in a mixture.

Preferred solvents are ethers such as dimethoxyethane, tetrahydrofuran and dioxane, hydrocarbons such as cyclohexane, toluene and xylene, alcohols such as ethanol, 1-propanol, 2-propanol, 1-butanol and tert-butanol, in each case individually or in a mixture.

In a particularly preferred variant of the process according to the invention, water, one or more water-insoluble and one or more water-soluble solvents are used, for example mixtures of water and dioxane, or water and tetrahydrofuran, or water, dioxane and ethanol, or water, tetrahydrofuran and methanol, or water, toluene and tetrahydrofuran, preferably water and tetrahydrofuran, or water, tetrahydrofuran and methanol.

The total amount of solvent is normally from 3000 to 500 g and preferably from 2000 to 700 g, per mole of the compound (II).

Appropriately, the process is carried out by adding the compound (II), the diphenyl-borinic acids (III), the base and the catalytic amount of the palladium catalyst to a mixture of water and one or more inert organic solvents, and stirring at a temperature of from 50° C. to 120° C., preferably from 70° C. to 110° C., more preferably from 90° C. to 100° C., for a period of from 1 to 50, preferably from 2 to 24 hours.

Depending on the solvent and temperature used, a pressure of from 1 bar to 6 bar, preferably from 1 bar to 4 bar, is established.

Preference is given to carrying out the reaction in water and tetrahydrofuran.

The reaction may be carried out in customary apparatus suitable for such processes.

On completion of reaction, palladium catalyst obtained as a solid is removed, for example by filtration, and the crude product is freed from the solvent or the solvents.

In the case of products which are not fully water-soluble, water-soluble palladium catalysts or complex ligands are removed fully from the crude product in the separation of the water phase.

Subsequently, further purification may be effected by methods which are known to those skilled in the art and are appropriate to the particular product, for example by recrystallization, distillation, sublimation, zone melting, melt crystallization or chromatography.

By the process according to the invention, it is possible to prepare, for example:
4'-chloro-2-nitrobiphenyl,
4'-chloro-2-aminobiphenyl,
4'-fluoro-2-nitrobiphenyl,
4'-fluoro-2-aminobiphenyl,
4'-methyl-2-nitrobiphenyl,
4'-methyl-2-aminobiphenyl,
4'-methoxy-2-nitrobiphenyl,
4'-methoxy-2-aminobiphenyl,
4'-bromo-2-nitrobiphenyl,
4'-bromo-2-aminobiphenyl,
3'-fluoro-2-nitrobiphenyl,
3'-fluoro-2-aminobiphenyl,
3'-chloro-2-nitrobiphenyl,
3'-chloro-2-aminobiphenyl,
3'-bromo-2-nitrobiphenyl,
3'-bromo-2-aminobiphenyl,
3'-methyl-2-nitrobiphenyl,
3'-methyl-2-aminobiphenyl,
3'-methoxy-2-nitrobiphenyl,
3'-methoxy-2-aminobiphenyl,
4'-phenyl-2-nitrobiphenyl,
4'-phenyl-2-aminobiphenyl,
4'-trifluoromethyl-2-nitrobiphenyl,
4'-trifluoromethyl-2-aminobiphenyl,
4'-fluoro-4-nitrobiphenyl,
4'-fluoro-4-aminobiphenyl,
4'-chloro-4-nitrobiphenyl,
4'-chloro-4-aminobiphenyl,
4'-bromo-4-nitrobiphenyl,
4'-bromo-4-aminobiphenyl,
4'-methyl-4-nitrobiphenyl,
4'-methyl-4-aminobiphenyl,
4'-cyano-4-nitrobiphenyl,
4'-cyano-4-aminobiphenyl,
2-nitrobiphenyl,
2-aminobiphenyl,
4-nitrobiphenyl,
4-aminobiphenyl.

The process according to the invention affords the compounds I in very high up to quantitative yields at very good purity.

The biphenyls obtainable by the process according to the invention are suitable as precursors for substituted biphenylamines, which are in turn intermediates for fungicidal crop protection active ingredients (cf., for example, EP-A 545 099).

Synthesis of 4'-chloro-2-nitrobiphenyl

EXAMPLE 1

Di-(4-Chlorophenyl)borinic acid

A solution of 120 g of trimethyl borate and 590 g of tetrahydrofuran was cooled to 11° C. To this were metered 1000 g of a 20% by weight solution of 4-chlorophenylmagnesium chloride in tetrahydrofuran within 2 hours. In the course of this, a temperature of 20-21° C. was established. After full addition, the reaction solution was stirred at 20° C. for another 1 hour.

The reaction mixture was subsequently treated with 621 g of 10% aqueous hydrochloric acid and stirred at 40° C. for 30 minutes. After phase separation, 1500 g of a solution of di(4-chlorophenyl)borinic acid in tetrahydrofuran were obtained (conversion 87%). The organic phase may be processed further as a crude product, or di(4-chlorophenyl)borinic acid may be isolated by column chromatography on silica gel using mixtures of ethyl acetate and cyclohexane.

EXAMPLE 2

Reaction of di(4-chlorophenyl)Borinic Acid and 1-chloro-2-nitrobenzene

An autoclave was initially charged with 240 g of a 20% by weight aqueous sodium hydroxide solution at 1 5-20° C. To this were metered 539 g of a 9-10% by weight solution of di(4-chlorophenyl)borinic acid in dioxane at 18-22° C. within 26 minutes. After full addition, the reaction solution was stirred at 18-22° C. for 40 minutes. 2.4 g of a 50% by weight solution of triphenylphosphine in dioxane were added to the reaction solution. After full addition, the reaction solution was stirred at 1 8-22° C. for 30 minutes. Finally, 117 mg of (bisacetonitrile)palladium(II) chloride and 84 g of 1-chloro-2-nitrobenzene were added to the reaction solution. The reaction solution was heated to 100° C. for 11.5 hours. In the course of this, an elevated pressure of 3.7 bar was established.

After full reaction of the di(4-chlorophenyl)borinic acid, the reaction solution was cooled to 40-45° C. and the pressure vessel was decompressed to standard pressure. The reaction solution was extracted with 250 g of 10% by weight aqueous hydrochloric acid. After phase separation, a solution of 4-chloro-2'-nitrobiphenyl in dioxane was obtained (conversion 99%). Dioxane was removed by distillation under reduced pressure and 4-chloro-2'-nitrobiphenyl could be isolated by melt crystallization.

EXAMPLE 3

Reaction of di(4-chlorophenyl)borinic acid and 1-chloro-2-nitrobenzene

An autoclave was initially charged with 495 g of a 20% by weight aqueous sodium hydroxide solution at 15-20° C. To this were metered 1000 g of an 11% by weight solution of di(4-chlorophenyl)borinic acid in tetrahydrofuran at 18-22° C. within 30 minutes. After full addition, the reaction solution was stirred at 18-22° C. for 30 minutes. 3.5 g of a 50% by weight solution of triphenylphosphine in tetrahydrofuran were added to the reaction solution. After full addition, the reaction solution was stirred at 20-21° C. for 30 minutes. Finally, 0.9 g of palladium(II) chloride in 227 g of molten 1-chloro-2-nitrobenzene were added to the reaction solution. The reaction solution was heated to 100° C. for 6-8 hours. In the course of this, an elevated pressure of 3.0 bar was established in the autoclave.

After full reaction of the di(4-chlorophenyl)borinic acid, the autoclave was decompressed to standard pressure and the reaction solution was cooled to 40-50° C. The reaction solution was extracted with 450 g of 10% by weight aqueous hydrochloric acid. After phase separation, a solution of 4-chloro-2'-nitrobiphenyl in tetrahydrofuran was obtained (conversion 99%).

EXAMPLE 4

Reaction of di-(4-chlorophenyl)borinic acid and 1-chloro-2-nitrobenzene

A 4 l four-necked flask was initially charged with 770 g of 22% by weight aqueous sodium hydroxide solution at 20° C. To this were metered 2045 g of a 13% by weight solution of di(4-chlorophenyl)borinic acid in tetrahydrofuran at 20° C. within 30 minutes. After full addition, the reaction solution was stirred at 20° C. for 30 minutes. 9.8 g of triphenylphosphine, 1.7 g of palladium(II) chloride and 273 g of molten 1-chloro-2-nitrobenzene were added to the reaction solution. The reaction solution was heated to reflux temperature for 20 hours.

After full reaction of the 4-chlorophenylboronic acid, the reaction solution was cooled to 40° C. and subsequently extracted with 255 g of 35% by weight aqueous hydrochloric acid. After phase separation, a solution of 4-chloro-2'-nitrobiphenyl in tetrahydrofuran was obtained (conversion 99%).

EXAMPLE 5

Reaction of 4-chlorophenylboronic acid and 1-chloro-2-nitrobenzene

A 4 m$^3$ reactor was initially charged with 1773 kg of a 13% by weight solution of 4-chlorophenylboronic acid in tetrahydrofuran at 18-22° C. Within 20 minutes, 538 kg of 25% by weight aqueous sodium hydroxide solution and 140 kg of water were metered in with stirring at 22-30° C. After full addition, the reaction solution was stirred at 22-25° C. for 30 minutes. 2.28 kg of triphenylphosphine, 372 g of palladium (II) chloride and 252 kg of molten 1-chloro-2-nitrobenzene were added to the reaction solution. The reaction solution was heated to 66° C. for 18 h. After full reaction of the 4-chlorophenylboronic acid, the reaction solution was cooled to 45° C. and extracted with 794 kg of 10% by weight aqueous hydrochloric acid. After phase separation, a solution of 4-chloro-2'-nitrobiphenyl in tetrahydrofuran was obtained (conversion 99%).

EXAMPLE 6

Reaction of di(4-chlorophenyl)borinic acid and 1-chloro-2-nitrobenzene

An autoclave was initially charged with 177 g of a 20% by weight aqueous sodium hydroxide solution at 15° C. To this were metered 415 g of a 9-10% by weight solution of di(4-chlorophenyl)borinic acid in tetrahydrofuran at 18-20° C. within 30 minutes. After full addition, the reaction solution was stirred at 18-20° C. for 30 minutes. 0.24 g of a 50% by weight solution of tri-tert-butylphosphine in tetrahydrofuran was added to the reaction solution. After full addition, the reaction solution was stirred at 18-20° C. for 30 minutes. Finally, 104 mg of a 10% by weight solution of palladium(II) chloride in 10% by weight aqueous hydrochloric acid and 91 g of an 85% by weight solution of 1-chloro-2-nitrobenzene in tetrahydrofuran were added to the reaction solution. The reaction solution was heated to 100° C. for 12 hours. In the course of this, an elevated pressure of 3.5 bar was established.

After full reaction of the di(4-chlorophenyl)borinic acid, the reaction solution was cooled to 40-50° C. and the pressure vessel was decompressed to standard pressure. The reaction solution was extracted with 125 g of 10% by weight aqueous hydrochloric acid. After phase separation, a solution of 4-chloro-2'-nitrobiphenyl in tetrahydrofuran was obtained (conversion 85%).

EXAMPLE 7

Reaction of di(4-chlorophenyl)borinic acid and 1-bromo-2-aniline

An autoclave was initially charged with 240 g of a 20% by weight aqueous sodium hydroxide solution at 20° C. To this were metered 539 g of a 9-10% by weight solution of di(4-chlorophenyl)borinic acid in tetrahydrofuran at 20° C. within 30 minutes. After full addition, the reaction solution was stirred at 20° C. for 30 minutes. 1.3 g of a 50% by weight solution of triphenylphosphine in tetrahydrofuran were added to the reaction solution. After full addition, the reaction solution was stirred at 20° C. for 30 minutes. Finally, 320 mg of a 10% by weight solution of palladium(II) chloride in 10% by weight hydrochloric acid and 108 g of an 85% by weight solution of 1-bromo-2-aniline in tetrahydrofuran were added to the reaction solution. The reaction solution was heated to 100° C. for 12 hours. In the course of this, an elevated pressure of 3.5 bar was established.

After full reaction of the di(4-chlorophenyl)borinic acid, the reaction solution was cooled to 40-50° C. and the pressure vessel was decompressed to standard pressure. After phase separation, the organic phase was extracted with 100 g of 20% by weight aqueous sodium hydroxide solution. A solution of 4-chloro-2'-nitrobiphenyl in tetrahydrofuran was obtained (conversion 85%). Tetrahydrofuran was removed by distillation under reduced pressure and 4-chloro-2'-nitrobiphenyl could be isolated by crystallization.

What is claimed is:

1. A process for preparing substituted biphenyls of the formula I

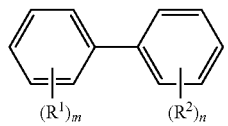

in which the substituents are defined as follows:
R$^1$ is nitro, amino or NHR$_3$,
R$^2$ is halogen,
R$^3$ is C$_1$-C$_4$-alkyl, C$_2$-C$_4$-alkenyl or C$_2$-C$_4$-alkynyl,
m is 1 or 2, where, in the case that m =2, the two R$^1$ radicals may have different definitions,
n is 1, 2 or 3, where, in the case that n =2 or 3, the two R$^2$ radicals may have different definitions,
which comprises reacting a compound of the formula II

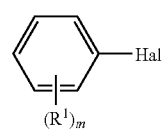

in which Hal is halogen and R$^1$ and m are each as defined above, in the presence of a base and of a palladium catalyst selected from the group of: a) palladium-triarylphosphine or palladium-trialkylphosphine complex with palladium in the zero oxidation state, b) salt of palladium in the presence of triarylphospine or trialkylphosphine as a complex ligand or c) metallic palladium, in the presence of triarylphosphine or trialkylphosphine, in a solvent, with a diphenylborinic acid (III)

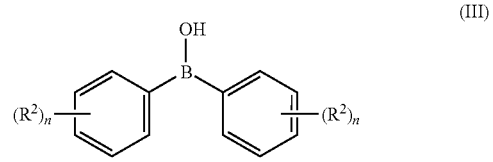

in which R$^2$ and n are each as defined above, where the triarylphosphines or trialkylphosphines used may be substituted.

2. The process according to claim 1, wherein the compound (II) used is 2-nitrochlorobenzene.

3. The process according to claim 1, wherein the starting compound (III) is a diphenylborinic acid which is substituted only in the 4-position.

4. The process according to claim 1, wherein a diphenylborinic acid (III) is used which bears, as the sole substituent in the 4-position, fluorine, chlorine or a methyl group.

5. The process according to claim 1, wherein the starting compound (III) is di(4-chlorophenyl)borinic acid.

6. The process according to claim 1, wherein the palladium catalyst a) used is tetrakis(triphenylphosphine)palladium or tetrakis(tri-tert-butylphosphine) palladium.

7. The process according to claim 1, wherein a palladium catalyst b) is used.

8. The process according to claim 7, wherein the salt of the palladium catalyst b) used is palladium chloride, palladium acetate or bisacetonitrilepalladium chloride.

9. The process according to claim 7, wherein a palladium catalyst b) is used for which from 6 to 60 equivalents of triphenylphosphine are used per equivalent of the palladium salt.

10. The process according to claim 1, wherein from 0.001 to 1.0 mol % of the palladium catalyst is used, based on the compound (II).

11. The process according to claim 1, wherein the reaction is carried out at a temperature of from 50 to 120° C.

12. The process according to claim 1, wherein the reaction is carried out in a mixture of water and an organic solvent.

13. The process according to claim 3, wherein the organic solvent used is an ether.

14. The process according to claim 1, wherein the reactions are carried out at a pressure of from 1 to 6 bar.

15. The process according to claim 2, wherein the starting compound (III) is a diphenylborinic acid which is substituted only in the 4-position.

16. The process according to claim 2, wherein a diphenylborinic acid (III) is used which bears, as the sole substituent in the 4-position, fluorine, chlorine or a methyl group.

17. The process according to claim 2, wherein the starting compound (III) is di(4-chlorophenyl)borinic acid.

18. The process according to claim 2, wherein the palladium catalyst a) used is tetrakis(triphenylphosphine)palladium or tetrakis(tri-tert-butylphosphine)palladium.

19. The process according to claim 3, wherein the palladium catalyst a) used is tetrakis(triphenylphosphine)palladium or tetrakis(tri-tert-butylphosphine)palladium.

20. The process according to claim 1, wherein the palladium c) is used and is metallic palladium applied to a support in the presence of triarylphosphine or trialkylphosphine.

21. The process according to claim 20, wherein the palladium catalyst c) used is metallic palladium on activated carbon in the presence of triphenylphosphine whose phenyl groups are substituted by a total of from 1 to 3 sulfonate groups.

* * * * *